United States Patent [19]
Chin

[11] Patent Number: 5,916,233
[45] Date of Patent: Jun. 29, 1999

[54] VESSEL HARVESTING METHOD AND INSTRUMENT INCLUDING ACCESS PORT

[75] Inventor: Albert K. Chin, Palo Alto, Calif.

[73] Assignee: Origin Medsystems, Inc., Menlo Park, Calif.

[21] Appl. No.: 09/035,704

[22] Filed: Mar. 5, 1998

[51] Int. Cl.⁶ .................................................. A61M 29/00
[52] U.S. Cl. ........................ 606/190; 606/194; 898/128
[58] Field of Search ................................. 606/190, 192, 606/194, 200; 898/128

[56] References Cited

U.S. PATENT DOCUMENTS

| | | | |
|---|---|---|---|
| 4,784,133 | 11/1988 | Mackin | 128/303.1 |
| 5,197,971 | 3/1993 | Bonutti | 606/192 |
| 5,271,380 | 12/1993 | Rick et al. | 128/4 |
| 5,334,150 | 8/1994 | Kaali | 604/164 |
| 5,569,291 | 10/1996 | Privitera et al. | 606/185 |
| 5,607,441 | 3/1997 | Sierocuk et al. | 606/190 |
| 5,630,813 | 5/1997 | Kieturakis | 606/46 |
| 5,667,520 | 9/1997 | Bonutti | 606/194 |
| 5,730,756 | 3/1998 | Kieturakis et al. | 606/196 |
| 5,738,628 | 4/1998 | Sierocuk et al. | 600/104 |
| 5,743,850 | 4/1998 | Moll et al. | 600/204 |

*Primary Examiner*—Michael Buiz
*Assistant Examiner*—Daphna Shai
*Attorney, Agent, or Firm*—Fenwick & West LLP

[57] ABSTRACT

A blunt dissection cannula and method selectively isolate a vessel of interest within the body of a patient by dissecting connective tissue in and about the adventitial tissue plane. The procedure includes selectively advancing the cannula and transparent tapered tip along the vessel of interior to form an insufflated cavity along the course of the vessel while visualizing the vessel and side branches within the field of view of an endoscope through the transparent tip. An electrocautery electrode selectively extends through an access port at the distal end of the cannula, eccentrically relative to the transparent tip, to facilitate visualizing rotational and translational positioning of the electrode to contact and electrocauterize side branches within the field of view through the transparent tip. A hook-shaped end of the electrode in contact with a cauterized side branch exerts severing tension on the cauterized side branch to isolate the vessel of interest within the insufflated cavity for subsequent transection and removal from the body of the patient.

17 Claims, 7 Drawing Sheets

VESSEL HARVESTING METHOD AND INSTRUMENT INCLUDING ACCESS PORT

RELATED APPLICATIONS

The subject matter of this application relates to the subject matter of pending application Ser. No. 08/907,691, entitled "Tissue Separation Cannula with Dissection Probe and Method," filed on Aug. 8, 1997 by Albert K. Chin.

FIELD OF THE INVENTION

This invention relates to vessel harvesting methods and cannula apparatus including a visualizing tip at a distal end for an endoscope within a lumen of the cannula, and including an access port at the distal end of the cannula aligned with another lumen of the cannula through which surgical instruments may be manipulated.

BACKGROUND OF THE INVENTION

Surgical techniques for harvesting a vessel of a patient include inserting a dissection cannula, having a tapered transparent tip, through an incision near the vessel for visually tracking the vessel while dissecting connective tissue in the adventitial plane along the surface of the vessel. A balloon disposed immediately proximate the tapered tip may be inflated to dilate a perivascular cavity to about 3 centimeters diameter. Following formation of a perivascular cavity in this manner, the incision may be sealed and insufflating gas may be supplied to maintain the cavity in expanded or dilated condition. A different form of cannula including a dissection tool may be inserted through a gas-sealing port into the insufflated cavity to occlude and sever side-branch vessels using clip appliers and electrocautery shears to isolate or skeletonize the target vessel from the side-branch vessels.

In vessel-harvesting surgical procedures of this type, successive inflation and deflation of the balloon as the cannula is advanced along the vessel extends operative time and is subject to balloon ruptures that necessitate replacement during the surgical procedure. In addition, the endoscope used to visualize the vessel during side-branch ligation and transection may become covered with blood and tissue and fluids that blur the visual images of the vessel and side branches, and that necessitates time-consuming withdrawal of the cannula for cleaning of the tip and endoscopic lens. Also, the separate types of cannulas for formation of a perivascular cavity and for side-branch transection contributes to the costs of the procedure and to the clutter of instruments assembled in the operating arena.

SUMMARY OF THE INVENTION

In accordance with the structural embodiment of the present invention, a single instrument performs the surgical functions according to the procedural embodiment of the invention previously performed using multiple, separate instruments. Specifically, the surgical instrument includes a transparent tapered tip attached at the distal end of a dissection cannula in sealing engagement with a lumen containing an endoscope and including an access port through the tip to facilitate access to surgical sites within the viewing field of the tip via instruments that can be introduced through other lumina of the cannula which are aligned with the access port. In this way, tissue may be dissected along the vessel of interest while being visualized through the transparent tapered tip, and surgical instruments may be introduced through the access port into a surgical site for surgical manipulations such as transections of side-branch vessels within the field of view, through the tapered tip, of an endoscope that is aligned therewith. The transparent tip forms a fluid-tight seal with a lumen in the cannula that houses the endoscope, and the access port through the tip aligns with another lumen of the cannula through which an electrocautery electrode or other surgical instrument may be introduced into a surgical site forward of the transparent tip and within the field of view therethrough. The transparent tip attaches in keyed orientation to the cannula to assure alignment of the tip and access port with respective lumina in the cannula for the endoscope and other surgical instruments.

DETAILED DESCRIPTION OF THE INVENTION

Figure 1A:
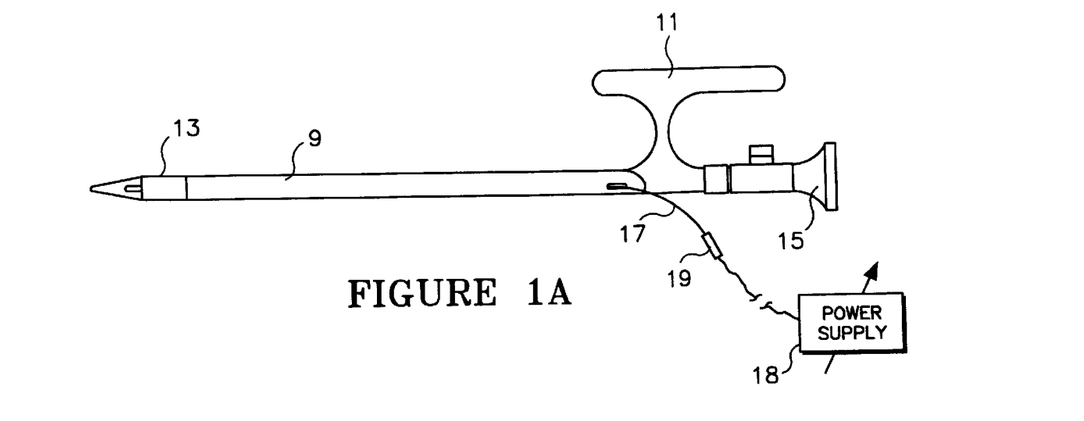
FIGS. 1A, 1B, 1C are pictorial side views of various configurations of one embodiment of the surgical instrument of the present invention.

Referring now to FIG. 1A, there is shown an elongated cannula 9 having a handle 11 attached thereto near the proximal end and including a transparent tapered tip 13 attached to the cannula 9 at the distal end thereof. The elongated cannula 9 includes multiple lumina therethrough between distal and proximal ends, including one lumen disposed to house in sliding relationship therein an endoscope having an eye piece 15 near the proximal end and having a viewport positionable within the tip 13 on the distal end. In addition, the cannula 9 may include another lumen containing a flexible, insulated electrocautery electrode 17 that may be rotated and translated within its lumen in response to manual manipulation of an attached finger grip 19 near the proximal end. The electrode 17 is connected to a power supply 18 for selectively applying high-voltage signal to the electrode to elctrocauterization of tissue in conventional manner. The electrocautery electrode 17 can protrude through an access port in the tip 13 to a position forward of the tip 13 in the field of view thereof. One or more additional lumina may also be disposed within the length of the cannula 9 in alignment with the access port in the tip 13 to facilitate introduction of additional surgical instruments into a surgical site within the field of view through the tapered transparent tip 13. The tapered tip 13 may be conveniently replaceable on the distal end of the cannula 9, as by sliding fit and snap-locking retention, and an aligning pin 21 may be disposed near the distal end of the cannula 9 for engaging a longitudinal slot in the tip 13 to assure proper alignment of the access port in the tip with the associated lumina in the cannula.

Figure 2A:
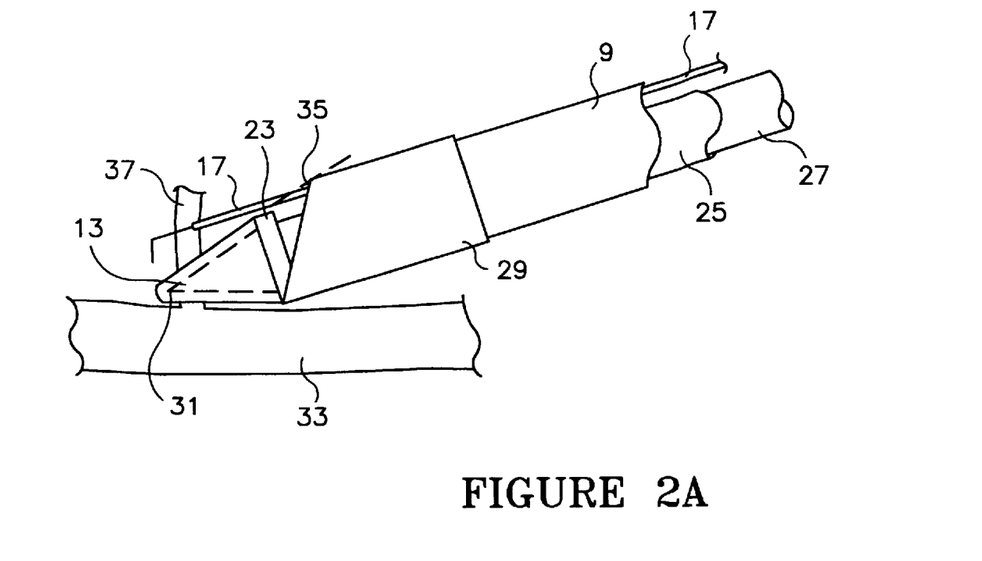
FIG. 2A is a pictorial side view of the transparent tip of the instrument of FIGS. 1A, 1B illustrated in use adjacent a vessel of interest.
Figure 2B:
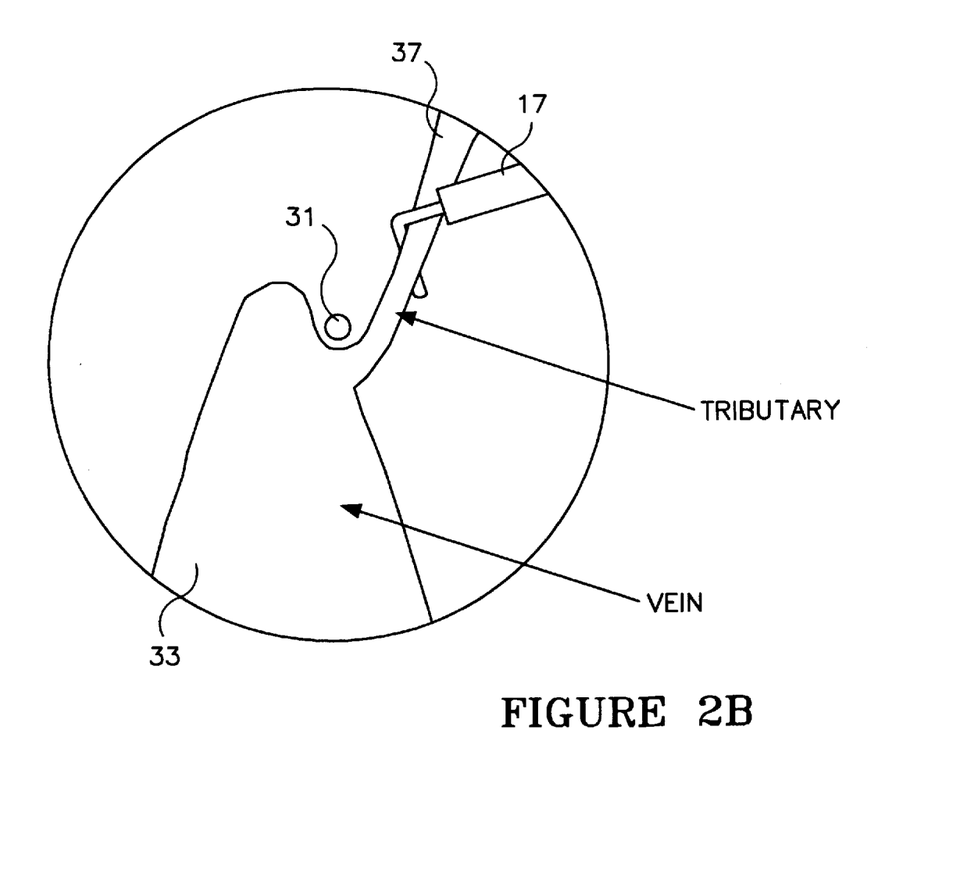
FIG. 2B is an endoscopic view through the transparent tip illustrated in FIG. 2A during transection of a side-branch vessel.

The transparent tapered tip 13, in the illustrated embodiments of FIGS. 2A and 3A, 3B, 3C, 4A, 4B, and 4C, includes an internal sealing rim 23 that forms a fluid-tight seal with the lumen 25 that contains the endoscope 27. The transparent tapered tip 13 may be incorporated into a ferrule-like collar 29 that fits in sliding engagement on the distal end of the cannula 9, and is formed with substantially conical outer walls that converge from about 12 mm diameter near the sealing rim 23 toward a tip that is rounded with approximately 0.040" radius. The conical side walls of the tip extend approximately 0.50" between the sealing rim 23 and the rounded tip, and internal walls of substantially uniform thickness similarly taper and converge at an internal cusp 31 to minimize the distortion of visualization through the tip 13, as shown in FIG. 2B. Thus, the endoscope 27 is sealed within the associated lumen 25 at the distal end thereof by the sealing rim 23 on the tapered transparent tip 13, and the viewport of the endoscope 27 may be retracted within the lumen 25 to a position of about 1 cm back from the cusp 31 of the internal walls. Visualization through the endoscope 27 and transparent tip 13 at a surgical site along a vein 33 such as the saphenous vein being harvested exhibits only minor distortion, as shown in FIG. 2B, as a result of the internal cusp 31 and rounded external tip that appear as only a small area of distortion in the field of view around the cusp 31 and rounded end of the tip 13.

Figure 1B:
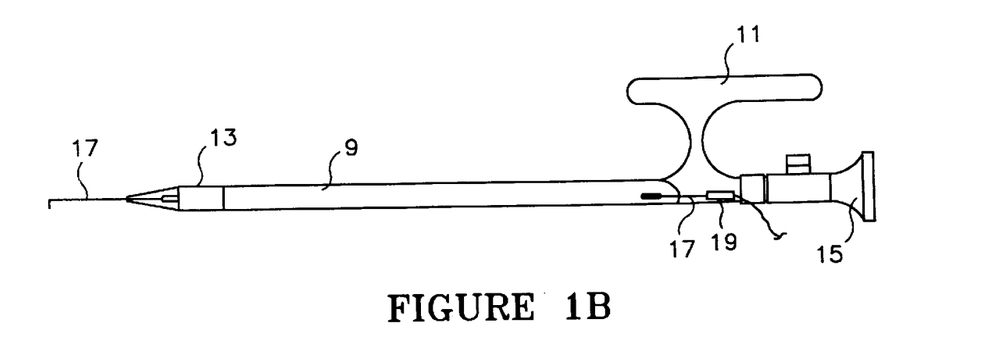
Figure 1C:
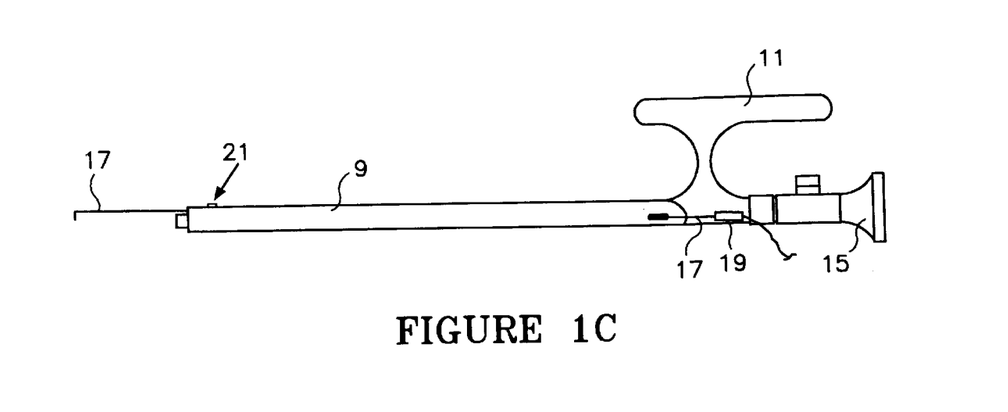

The access port 35 that is formed eccentric the transparent tip 13 aligns with one or more lumina within the cannula 9 to facilitate projection of surgical instruments forward of the tip 13 into the field of view therethough. Thus, as shown in FIG. 2A, an electrocautery electrode 17 including a hook-like configuration at the distal end thereof may selectively protrude through the access port 35 into the field of view through the tip 13, as shown in FIG. 2B. The conical exterior wall of the tip 13 may be placed against a vessel of interest, and advanced therealong with clear vision of the course along the vessel 33 and around side branch vessels 37 as the cannula assembly is advanced along the vessel 33 to bluntly dissect connective tissue from the vessel. The conically tapered walls of the tip 13 conveniently facilitate dissection of connective tissue in and above and below adventitial tissue planes around the vessel 33 or around side branch vessels 37 that are encountered along the course of the vessel. For such dissection procedures, the distal end of the cannula 9 may be configured with no protruding instruments, such as electrocautery electrode 17, to facilitate bluntly dissecting tissue from all sides of the vessel by progressively advancing the rounded end of the tapered tip 13 along the course of the vessel on all sides thereof to thereby form a working cavity about the detached vessel. Upon encountering a side-branch vessel 37, the rounded end of transparent tip 13 assures that such vessel will not be punctured and that visualization of the site can be preserved as the distal end of the cannula 9 is reconfigured for example, by projecting forward the electrocautery electrode 17 through the access port 35, as illustrated in FIGS. 1B and 2A. In this configuration, the electrode 17 including a hook-like distal end, may be rotated and translationally positioned about the side branch vessel 17, as shown in FIGS. 2A and 2B, to electrocauterize the vessel in conventional manner upon application of high-voltage electrical signal to the electrode 17 from power supply 18. The side branch vessel 37 thus cauterized may be severed from the vessel of interest 33 by forceably retracting the electrode 17 with the hook-like distal end engaged around the side branch vessel 37, as shown in FIGS. 2A and 2B, to sever the cauterized side branch vessel under the rupturing tension of mechanical pulling at the cauterized site. Alternatively, conventional cauterizing shears may be introduced into the surgical site at a side branch vessel through another lumen in the cannula 9 that aligns with the access port 35, and such shears may be used to cut and cauterize the side branch vessel 37 from the vessel of interest 33.

Figure 3A:
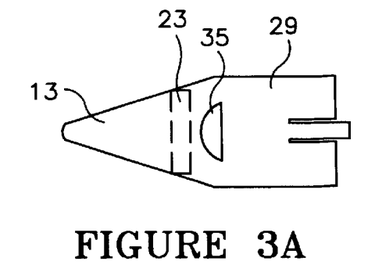
FIGS. 3A, 3B, 3C are top and side and end views, respectively, of a tip for the surgical instrument of FIG. 1A, 1B, 1C showing asymmetrically tapered walls containing an access port and an attaching lock.
Figure 3B:
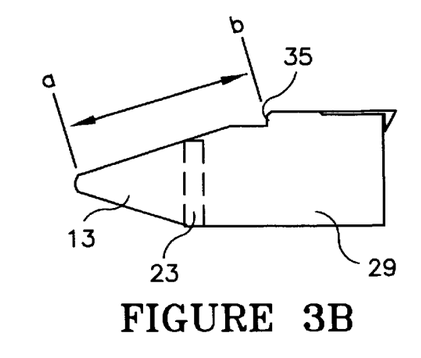
Figure 3C:
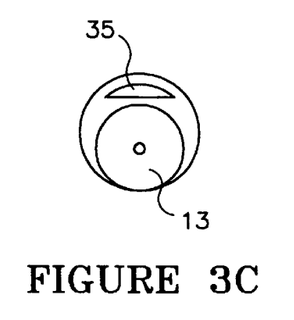
Figure 4A:
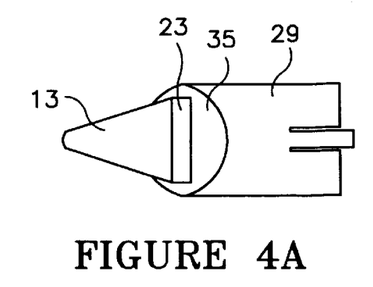
FIGS. 4A, 4B, 4C are top and side and end views, respectively, of a tip for the surgical instrument of FIG. 1A, 1B, 1C showing a beveled access port surrounding the transparent tip.
Figure 4B:
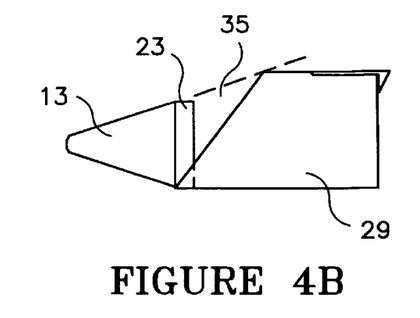
Figure 4C:
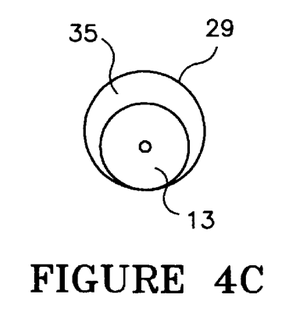

The tapered tip 13 has an essentially smooth profile along the external conical wall to permit positioning of the conical wall flat against the vessel of interest in any orientation. For this reason, the access port 35 is preferably recessed within the profile of the conical wall of the tip 13, as illustrated in FIGS. 2A, 3A, 3B, 3C, 4A, 4B, and 4C, to facilitate tracking the vessel within the specific peri-adventitial plane for dilating the dissected plane into a working cavity, typically of about 20 mm diameter about the vessel 33. The access port 35 may include a small port within the conical wall of the tapered tip, as illustrated in FIGS. 3A, 3B, and 3C, or may constitute substantially the entire eccentric differential area between the outer collar 29 and the sealing rim 23 of the tapered tip 13, as illustrated in FIGS. 2A, and 4A, 4B, and 4C. Larger access ports 35 aligned with additional lumina in the cannula 9 can accommodate additional surgical instruments such as cauterizing shears, clip appliers, suture loop, and the like, for introduction into the surgical site forward of the tapered tip 13. Sliding seals may be incorporated in each lumen to maintain gas-tight integrity around surgical instruments introduced through the cannula 9 in support of insufflation with gas under pressure of a working cavity thus formed around the vessel of interest 33. The cannula 9 may be rotated about the axis of the endoscope 27 to facilitate blunt dissection of tissue around all sides of the vessel of interest 33, and to extend the orbital positioning of the electrocautery electrode 17 relative to the axis of the endoscope. The tapered tip 13 and associated collar 29 may be slide-fitted onto the distal end of the cannula 9, keyed or splined into proper alignment between access port 35 and associated lumina, for example, by aligning pin 21 within a mating slot in the collar 29. The tip 13 may be latched to the distal end of the cannula 9, for example, by a locking clip 41, as illustrated in FIGS. 4B and 4C, that mates with a recess or aperture near the distal end of the cannula 9. In this way, tips may be changed conveniently as blood and tissue accumulate on the transparent tapered tip 13.

Figure 5:
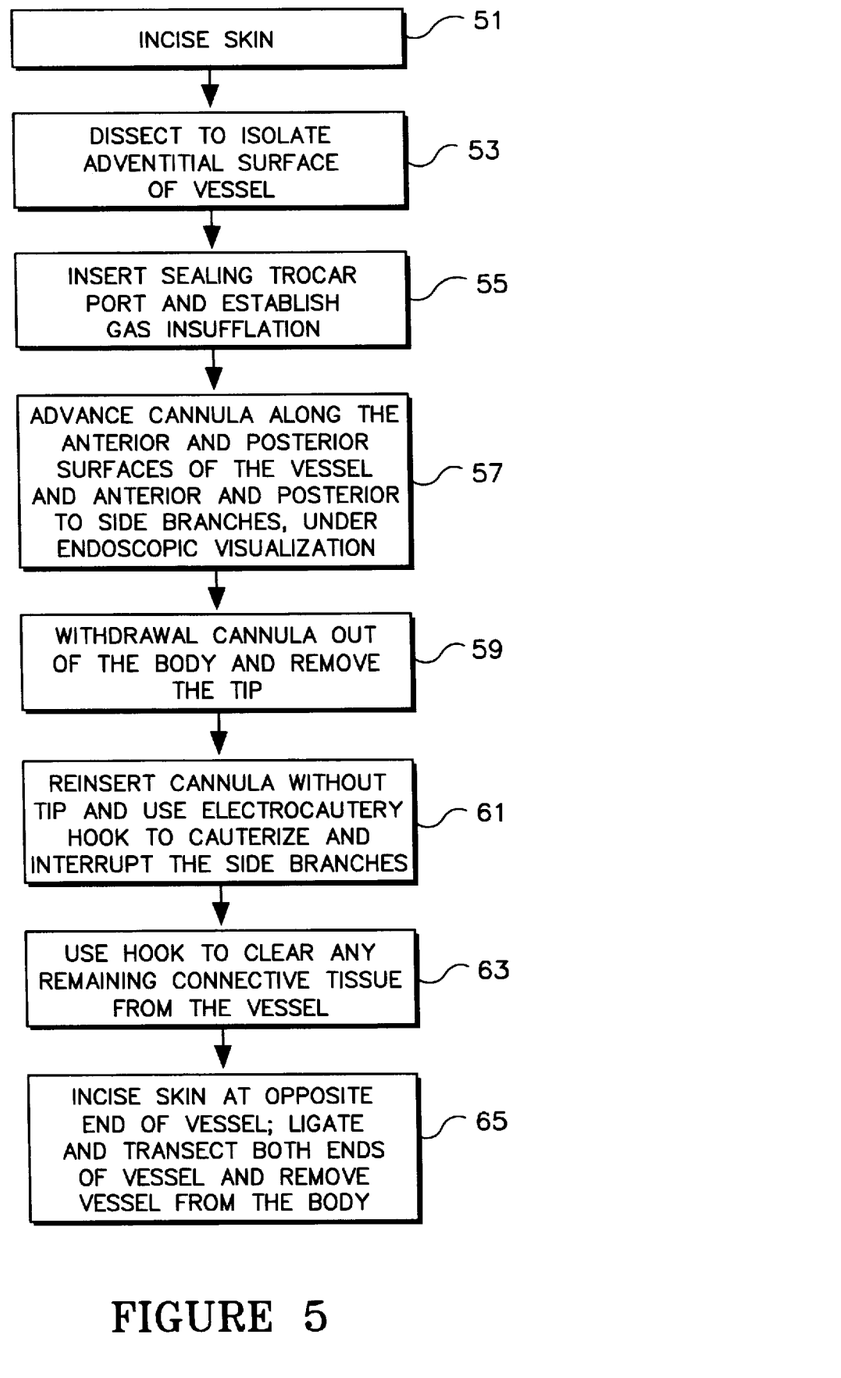
FIGS. 5–8 are flow charts illustrating various embodiments of the surgical procedure according to the present invention.
Figure 6:
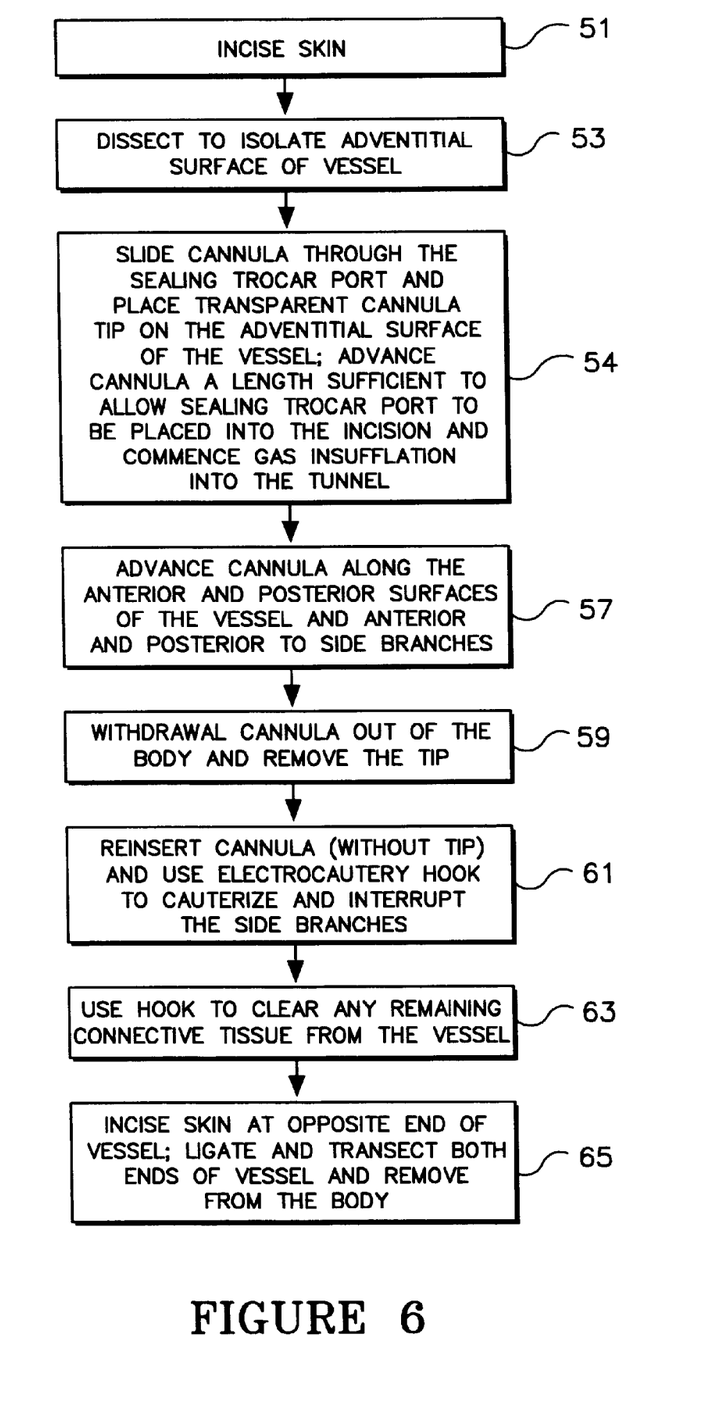

In operation, the tapered tip and cannula configured according to embodiments of the invention as illustrated and described above may be used to perform the surgical procedure as set forth in the flow chart of FIG. 5. Specifically, a small incision is formed 51 over the vessel of interest to isolate 53 the adventitial layer of the vessel. A trocar port may be positioned in the incision to establish insufflation 55. Alternatively, the trocar port may be positioned near the proximal end of the cannula, and blunt dissection may then proceed by advancing the tapered tip 13 along the vessel and the adventitial layer about the vessel until the trocar port can be slid forward on the cannula and positioned 54 in the incision to establish insufflation, as illustrated in FIG. 6.

The transparent tapered tip is placed in contact with the exposed surface of the vessel and is advanced several centimeters 57 along anterior and posterior surfaces of the vessel under direct visualization through the transparent tapered tip to create a perivascular cavity adjacent the vessel of interest. The trocar port in the incision may be a balloon port, such as the BTT (Blunt Tip Trocar that is commercially available from Origin Medsystems, Inc. of Menlo Park, Calif.). Alternatively, the trocar port may be a tapered port of conventional configuration with external threads. The trocar port seals the incision and allows gas to be insufflated into the perivascular cavity. A gas such as carbon dioxide may be instilled at approximately 10 mm Hg pressure into the cavity, distending the cavity and allowing visualization of the dissected vessel and side branches. The cannula is used to probe both anterior and posterior surfaces of the vessel and its side branches, and to separate the vessel from adjoining connective tissue, leaving the vessel suspended within the formed cavity. Side branches are thus exposed within the cavity, making it simple to cauterize and transect them, using the hook-like electrocautery probe as previously described.

Figure 7:
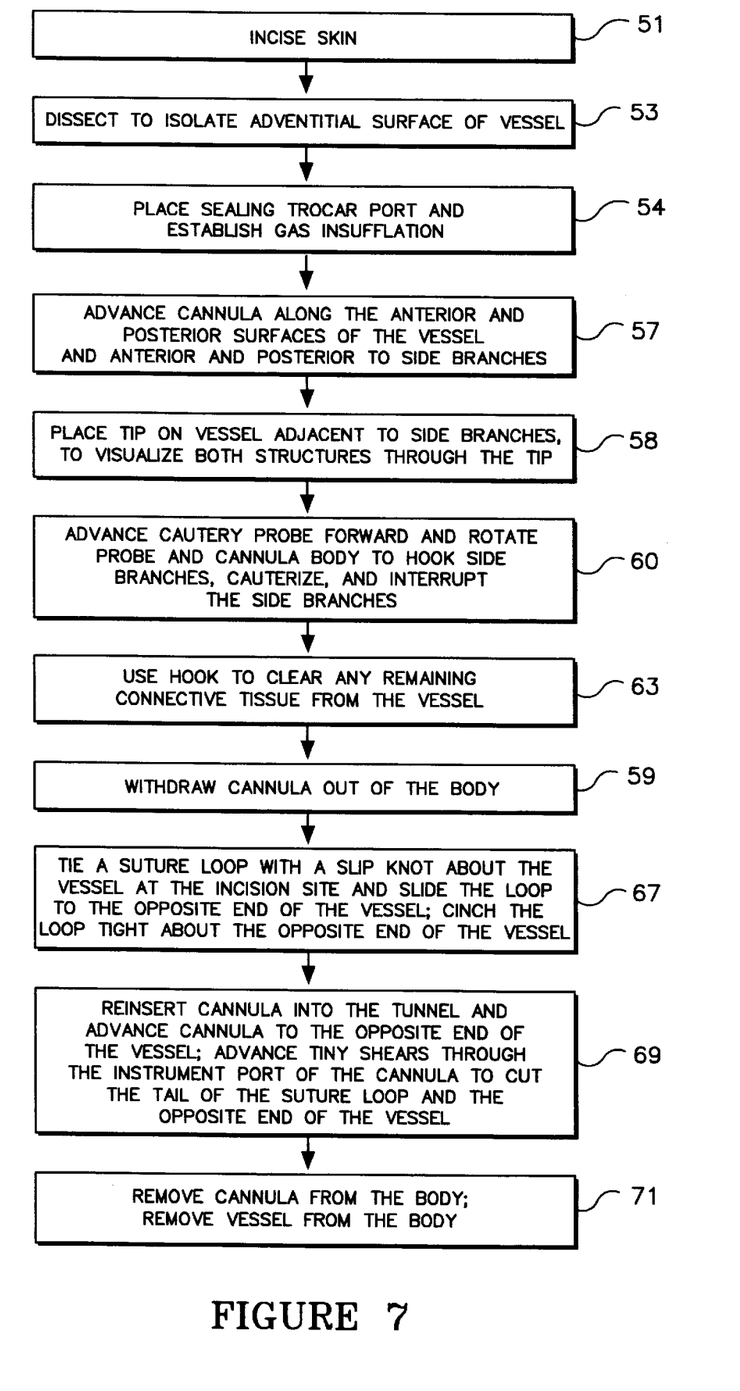

Following isolation of the vessel and its tributaries or side branches as a result of successive advances of the cannula along the vessel, the cannula may be withdrawn through the trocar port as desired to remove or replace the transparent tapered tip, and the cannula may be reinserted 61, with or without the transparent tapered tip in place, and the hook-like electrocautery probe may be advanced to cauterize and transect the side branches. The probe is hooked around a side branch, and high-voltage electrical signal is applied to coagulate the side branch in conventional manner. Tension is applied to the probe to transect the side branch in the cauterized region. The hook-like electrocautery electrode may also be used to clear any remaining connective tissue 63. Transection of all side branches is followed by ligation and transection of the main trunk of the vessel to facilitate its removal from the perivascular cavity. The vessel may be ligated and transected via a separate incision at the transection site for removal from the cavity 65. Alternatively, a suture noose with a slip knot such as a Roeder's knot may be looped around the vessel near the site of the initial incision. The noose is then pushed forward to the transection site and tightened around the vessel of interest 67, as illustrated with reference to the flow chart of FIG. 7. The noose is cut off near the ligation site using 1 mm shears that can be advanced 69 through a small instrument lumen and the access port in the tip of the cannula, and the ligated vessel may then be removed from the cavity 71 through the initial incision.

Figure 8:
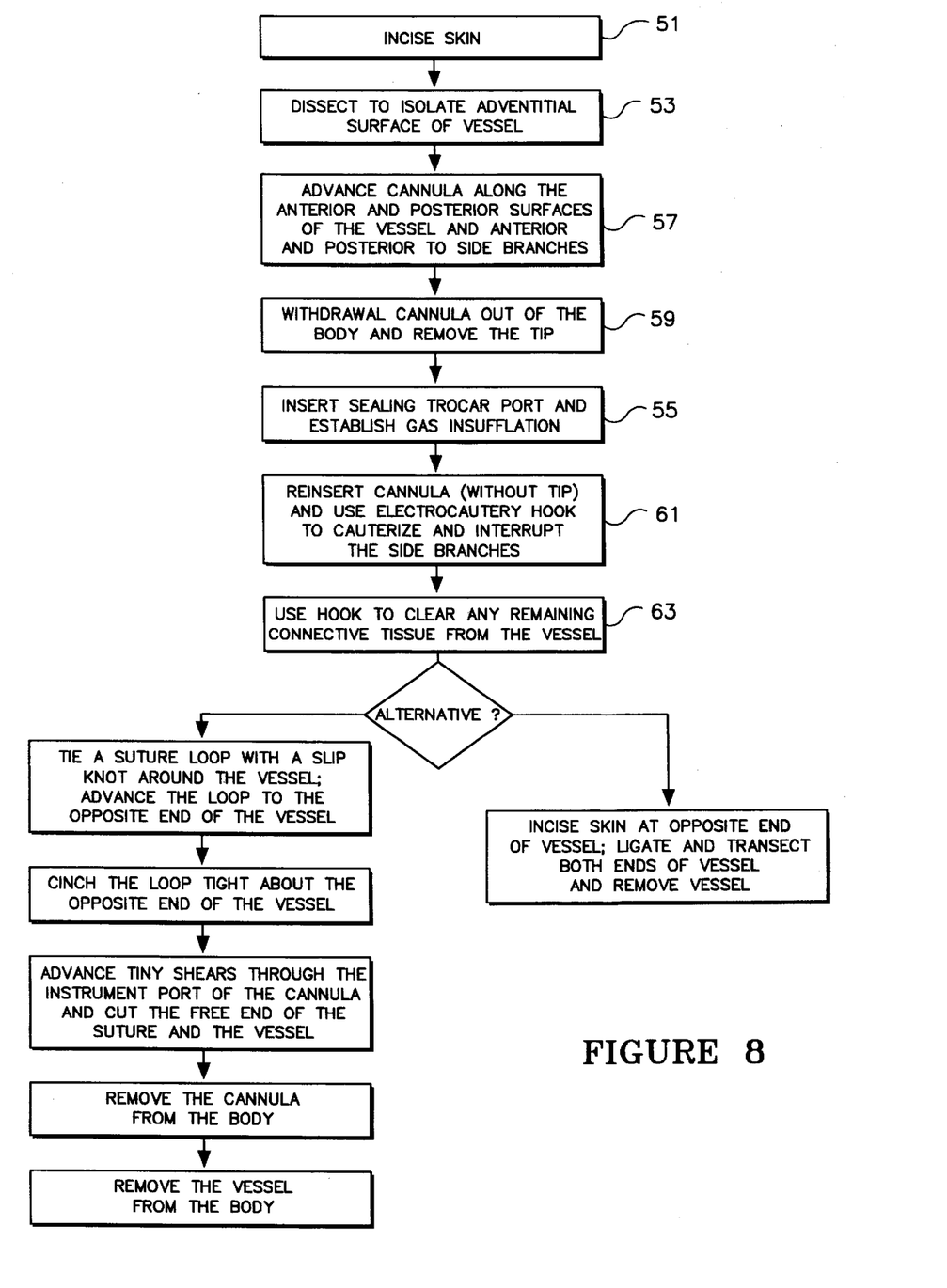

As illustrated in the flow chart of FIG. 8, the cannula of the present invention may be used with variations in the procedure, including in the sequence of placing the trocar port in the initial incision in order to establish insufflation at a desired phase in the vessel-harvesting procedure. Also, variations are possible in the technique by which the isolated vessel of interest is removed from the cavity, either by incising the skin down to the working cavity at a location along the vessel remote from the initial incision to facilitate transecting the vessel at both ends 73, or by slipping a suture loop along the vessel through the initial incision to be tightened around a remote location along the vessel in the manner as previously described.

If blood and tissue fluid in the cavity, or tunnel, smudge the lens of the endoscope, the tip may be selectively removed and reattached to the cannula for the phase of the procedure in which the tributaries are cauterized and transected. FIG. 2 shows the device used to transect a tributary while the tip is attached to the cannula. The transparent tapered portion of the tip is placed against the vein 33 and the tributary 37 lies against the side of the transparent tapered tip. As seen in the endoscope view depicted in FIG. 2, placement of the tip against both vessel and side branch displaces blood away from the interface between the tip, the vessel, and the side branch, and facilitates viewing both vessel and side branch within the endoscopic field of view. The electrocautery probe may be advanced and hooked around each tributary within the clear visualization provided through the tip so that a vessel and its tributary may be cauterized and transected in a safe manner according to one or more of the procedural steps previously described.

Therefore, the apparatus and method of the present invention obviate the need for successive inflation and deflation of a distal balloon in order to form a working cavity about a vessel being harvested. Multiple lumina in an elongated cannula house an endoscope and other surgical instruments, and a transparent tapered tip at the distal end of the cannula is sealed about the lumen that houses the endoscope, while other lumina align with an access port through the tip to permit introduction of surgical instruments through the cannula into the field of view of the endoscope forward of the transparent tip.

What is claimed is:

1. Surgical apparatus comprising:
   an elongated cannula having a proximate end and a distal end, and including plural lumina extending within the cannula between the ends thereof;
   an endoscope disposed within one of the plural lumina and extending from an eyepiece near the proximal end to a viewport near the distal end;
   a dissection tip attached to the distal end of the cannula substantially about the outer perimeter thereof and including a transparent tapered tip attached thereto in alignment with the viewport of the endoscope in said one of the plural lumina to permit visualization through the transparent tip within a field of view forward thereof, the dissection tip including an access port aligned with another of said plural lumina to permit protrusion therethrough of a surgical instrument into said field of view forward of the transparent tapered tip in a position of alignment with the viewport of the endoscope, and wherein the transparent tapered tip includes substantially conical outer walls which converge from a rim that mates with the distal end of the cannula towards a rounded end, and includes inner substantially conical walls that converge from the rim to a sharp point that is substantially axially aligned with the rounded end on the outer walls to reduce visual distortion within said field of view.

2. Surgical apparatus as in claim 1 in which the rim is disposed in fluid-tight sealing engagement with said one of the plural lumina in alignment with the viewport of the endoscope.

3. Surgical apparatus as in claim 2 in which said dissection tip includes locking apparatus for releasably securing the dissection tip to the distal end of the cannula.

4. Surgical apparatus as in claim 1 in which said one of the plural lumina is eccentric an elongation axis of the cannula, and said transparent tapered tip aligned with a viewport of the endoscope is eccentric said axis, and said access port is also eccentric said axis.

5. Surgical apparatus as in claim 1 in which the access port is disposed within substantially the differential area between the outer perimeter of the cannula at the distal end thereof, and the outer conical wall of the transparent tapered tip.

6. Surgical apparatus as in claim 5 in which the electrode includes a hook-like remote end that is disposed to selectively protrude and retract through the access port for positioning of said remote end within the field of view through the transparent tapered tip.

7. Surgical apparatus as in claim 1 including an elongated electrode slidably and rotatably disposed within another of the plural lumina aligned with the access port for selective extension and rotation of the electrode in protrusion through the access port.

8. Surgical apparatus as in claim 7 in which said electrode is electrically insulated substantially between ends thereof, and is electrically coupled to a supply of high voltage electrical signal.

9. Surgical apparatus according to claim 1 in which the access port is disposed within a projection of the conical walls of the tapered tip toward the outer perimeter of the distal end of the cannula.

10. Surgical apparatus as in claim 1 in which the conical wall of the transparent tapered tip between rim and rounded end is approximately 0.50 inches and the rounded end includes a radius of approximately 0.040 inches.

11. A method of harvesting a vessel of interest from within the body of a patient, using an elongated cannula containing an endoscope and including a transparent, tapered, tissue-dissecting tip at the distal end of the cannula, the cannula including an elongated instrument disposed within the cannula, the cannula including an elongated instrument disposed within the cannula the method comprising:

forming an incision in the body of the patient to expose the vessel of interest;

sealing the incision in gas-tight relationship about the cannula to support insufflation with gas under pressure about the vessel of interest;

selectively advancing the tip along the course of the vessel of interest in contact with anterior and posterior surfaces thereof to dissect connective tissue therefrom within a field of view of the endoscope through the transparent tip to form an insufflated cavity about the vessel of interest; and selectively extending an end of the elongated instrument from the distal end of the cannula into the field of view of the endoscope through the transparent tip through an access port to selectively position the end of the elongated instrument in contact with a tributary of the vessel of interest as visualized through the endoscope.

12. The method according to claim 11 including an electrocautery electrode as the elongated instrument within the cannula, the method comprising:

selectively extending the electrode from the distal end of the cannula in eccentric orientation relative to the endoscope to position a remote end of the electrode in contact with a tributary vessel within the field of view of the endoscope.

13. The method performed according to claim 12 with a hook-shaped remote end of the electrode, the method comprising:

selectively electrocauterizing the tributary vessel at a location thereon away from the vessel of interest; and retracting the electrode toward the distal end of the cannula with the hook-shaped remote end within the field of view of the endoscope and engaged with the tributary vessel to exert severing tension thereon substantially at the cauterized location.

14. The method according to claim 12 comprising:

transecting the isolated vessel of interest at spaced locations therealong within the insufflated cavity; and removing the transected vessel of interest from the body of the patient.

15. The method according to claim 13 comprising:

forming another incision spaced from the initial incision along the course of the vessel of interest; and the transecting of the isolated vessel of interest is performed within said initial and another incision for removal from the body of the patient through one of said incisions.

16. The method according to claim 13 comprising:

forming a suture loop about the isolated vessel of interest including a slip knot near the initial incision;

transferring the suture loop along the vessel of interest to a location therealong remote from the initial incision;

tightening the suture loop and slip knot about the vessel of interest at the remote location prior to transecting and removing the vessel of interest from the body of the patient.

17. The method according to claim 11 in which a plurality of tributary vessels are severed from the vessel of interest by multiply electrocauterizing and severing under tension each such tributary vessel to isolate the vessel of interest within the insufflated cavity.

* * * * *